(12) United States Patent
Connelly

(10) Patent No.: US 9,381,118 B1
(45) Date of Patent: Jul. 5, 2016

(54) EYE, FACE, AND HEAD WEAR

(76) Inventor: William L. Connelly, Kingman, AZ (US)

( * ) Notice: Subject to any disclaimer, the term of this patent is extended or adjusted under 35 U.S.C. 154(b) by 366 days.

(21) Appl. No.: 13/523,880

(22) Filed: Jun. 14, 2012

Related U.S. Application Data

(60) Provisional application No. 61/497,015, filed on Jun. 14, 2011.

(51) Int. Cl.
*A61F 9/02* (2006.01)

(52) U.S. Cl.
CPC ...................................... *A61F 9/028* (2013.01)

(58) Field of Classification Search
CPC ........... A61F 9/02; A61F 9/027; A42B 3/185; G02C 5/006
USPC .............. 2/426–429, 436–437; 351/41; 442/1
See application file for complete search history.

(56) References Cited

U.S. PATENT DOCUMENTS

| | | | | | |
|---|---|---|---|---|---|
| 1,562,350 | A | * | 11/1925 | Luckey | 52/172 |
| 4,149,276 | A | * | 4/1979 | Castro | 2/437 |
| 4,288,878 | A | * | 9/1981 | Helmbreck | 2/427 |
| 4,556,995 | A | * | 12/1985 | Yamamoto | 2/439 |
| 4,856,120 | A | * | 8/1989 | Hart | 2/428 |
| 5,129,109 | A | * | 7/1992 | Runckel | 2/440 |
| 5,224,772 | A | * | 7/1993 | Fustos | 362/105 |
| 5,371,555 | A | * | 12/1994 | Nagel | 351/57 |
| 5,517,700 | A | * | 5/1996 | Hoffman | 2/428 |
| 5,564,130 | A | * | 10/1996 | Feng | 2/428 |
| 5,572,989 | A | * | 11/1996 | Lutz et al. | 128/201.18 |
| 5,617,588 | A | * | 4/1997 | Canavan et al. | 2/428 |
| 5,860,168 | A | * | 1/1999 | Winefordner et al. | 2/428 |
| 6,009,564 | A | * | 1/2000 | Tackles et al. | 2/436 |
| 6,131,246 | A | * | 10/2000 | Paulson et al. | 24/265 BC |
| 6,195,808 | B1 | * | 3/2001 | Huang | 2/428 |
| 6,233,342 | B1 | * | 5/2001 | Fernandez | A61F 9/028 2/235 |
| 6,276,794 | B1 | * | 8/2001 | Chiang | 351/43 |
| 6,415,447 | B1 | * | 7/2002 | Frazier | 2/165 |
| 6,477,717 | B1 | * | 11/2002 | Winefordner et al. | 2/428 |
| 6,611,966 | B1 | * | 9/2003 | Yamamoto et al. | 2/436 |
| 6,698,033 | B2 | * | 3/2004 | Fujima | 2/428 |
| 7,146,654 | B2 | * | 12/2006 | Chiang | 2/428 |
| 7,181,779 | B2 | * | 2/2007 | Hussey | 2/436 |
| 7,865,977 | B2 | * | 1/2011 | Rayl et al. | 2/435 |
| 7,979,765 | B2 | * | 7/2011 | Wen et al. | 714/738 |
| 2001/0029623 | A1 | * | 10/2001 | Tsubooka | 2/436 |
| 2003/0056281 | A1 | * | 3/2003 | Hasegawa | 2/428 |
| 2004/0179166 | A1 | * | 9/2004 | Jannard et al. | 351/41 |
| 2006/0085882 | A1 | * | 4/2006 | Broersma | 2/9 |
| 2007/0169252 | A1 | * | 7/2007 | Rayl et al. | 2/435 |

(Continued)

*Primary Examiner* — Robert J Hicks
*Assistant Examiner* — Timothy K Trieu
(74) *Attorney, Agent, or Firm* — Booth Udall Fuller, PLC

(57) ABSTRACT

Eye, face, and head wear is disclosed. The eye, face, or head wear may include a frame. A lens or a shield may be associated with the frame. At least one semipermeable membrane vent may be disposed in the frame, the lens, or the shield. At least one sliding air intake vent may be included in a bottom of the frame. The frame may include a frame assembly including a sub-frame and a member over-molded onto the sub-frame. The member over-molded onto the sub-frame may also be over-molded onto an edge of the lens or the shield. An inflatable face seal or an inflatable nose seal may be coupled to the frame. The frame may further include a perforated forehead section and a semipermeable membrane vent disposed therein. A strap may be included, as well as at least one strap spool assembly for adjusting the strap.

9 Claims, 12 Drawing Sheets

(56) References Cited

U.S. PATENT DOCUMENTS

| | | | |
|---|---|---|---|
| 2008/0176468 A1* | 7/2008 | Chen | 442/1 |
| 2009/0038061 A1* | 2/2009 | Shiue | 2/440 |
| 2009/0113607 A1* | 5/2009 | Lian | 2/427 |
| 2010/0005575 A1* | 1/2010 | Dondero | 2/428 |
| 2010/0064421 A1* | 3/2010 | Wang-Lee | 2/428 |

* cited by examiner

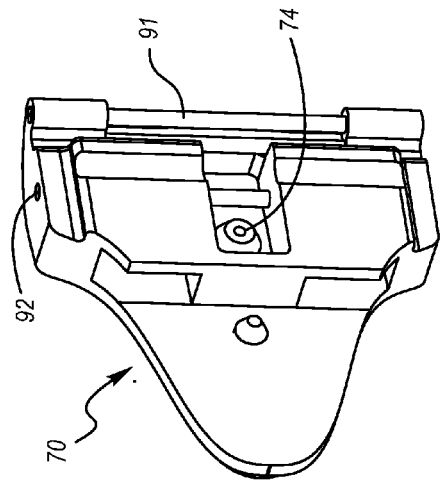
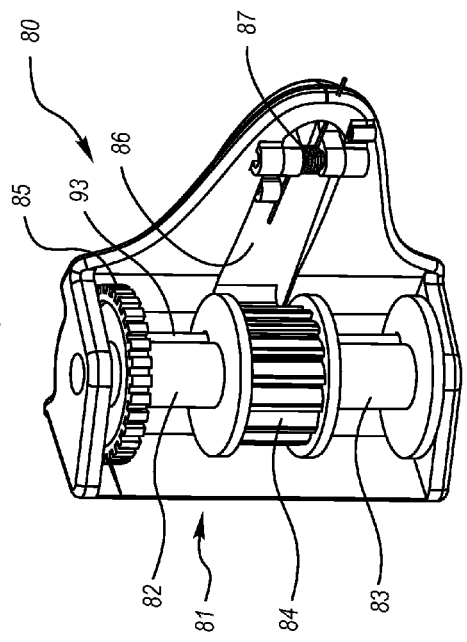
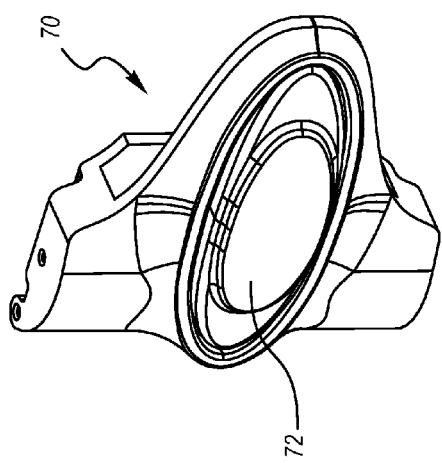
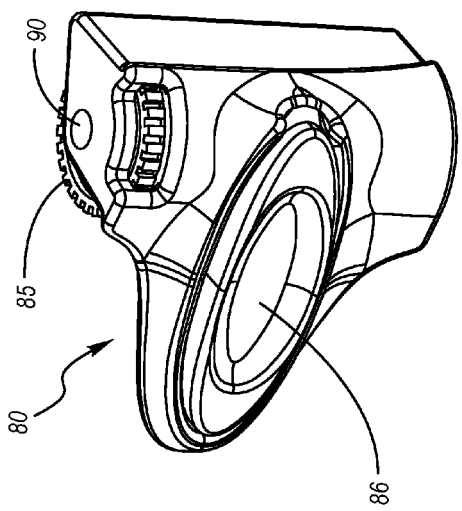
Fig. 10A
Fig. 10B
Fig. 11A
Fig. 11B

EYE, FACE, AND HEAD WEAR

CROSS REFERENCE TO RELATED APPLICATIONS

This application claims the benefit of the filing date of U.S. Provisional Patent Application No. 61/497,015, filed on Jun. 14, 2011, the disclosure of which being hereby incorporated entirely herein by reference.

BACKGROUND

1. Technical Field

This document relates generally to eye, face, and head wear.

2. Background

It is desirable to design new eye, face, and head wear that has features, components, and properties lacking in conventional products.

SUMMARY

Aspects of this document relate to eye, face, and head wear. These aspects may comprise, and implementations may include, one or more or all of the components and steps set forth in the appended CLAIMS, which are hereby incorporated by reference.

Eye, face, and head wear is disclosed. The eye, face, or head wear may include a frame. A lens or a shield may be associated with the frame. At least one semipermeable membrane vent may be disposed in the frame, the lens, or the shield.

Particular implementations may include one or more or all of the following.

The at least one semipermeable membrane vent may be formed of expanded polytetrafluoroethylene. The at least one semipermeable membrane vent may be a GORE™ Protective Vent.

At least one sliding air intake vent may be included in a bottom of the frame. The at least one semipermeable membrane vent may be incorporated into the at least one sliding air intake vent.

The at least one semipermeable membrane vent may include at least two semipermeable membrane vents, one disposed in the frame and one disposed in the lens or the shield.

The frame may include a frame assembly including a sub-frame and a member over-molded onto the sub-frame. The member over-molded onto the sub-frame may be formed of a thermoplastic elastomer. The thermoplastic elastomer may be VERSAFLEX™ OM 9-802CL. The member over-molded onto the sub-frame may also be over-molded onto an edge of the lens or the shield.

An inflatable face seal may be coupled to the frame. Alternatively, an inflatable nose seal may be coupled to the frame.

The frame may further include a perforated forehead section and a semipermeable membrane vent disposed therein.

A strap may be included, as well as at least one strap spool assembly for adjusting the strap, the at least one strap spool assembly coupled to the strap and the sub-frame. The at least one strap spool assembly may include two strap spool assemblies. One may be coupled to one side of the sub-frame and the other may be coupled to an opposing side of the sub-frame.

The strap may be over-molded to the sub-frame.

The foregoing and other aspects, features, and advantages will be apparent to those of ordinary skill in the art from the DESCRIPTION and DRAWINGS, and from the CLAIMS.

BRIEF DESCRIPTION OF DRAWINGS

Implementations are illustrated by way of example, and not by way of limitation, in the figures of the accompanying DRAWINGS and in which like elements refer to similar elements.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of implementations.

FIG. 10A is a front perspective view of a pump assembly of the goggles implementation of FIG. 1;

FIG. 10B is a rear perspective view of the pump assembly of the goggles implementation of FIG. 1;

FIG. 11A is a front perspective view of a spool assembly of the goggles implementation of FIG. 1;

FIG. 11B is a rear perspective view of the spool assembly of the goggles implementation of FIG. 1;

DETAILED DESCRIPTION

Overview

Figure 1:
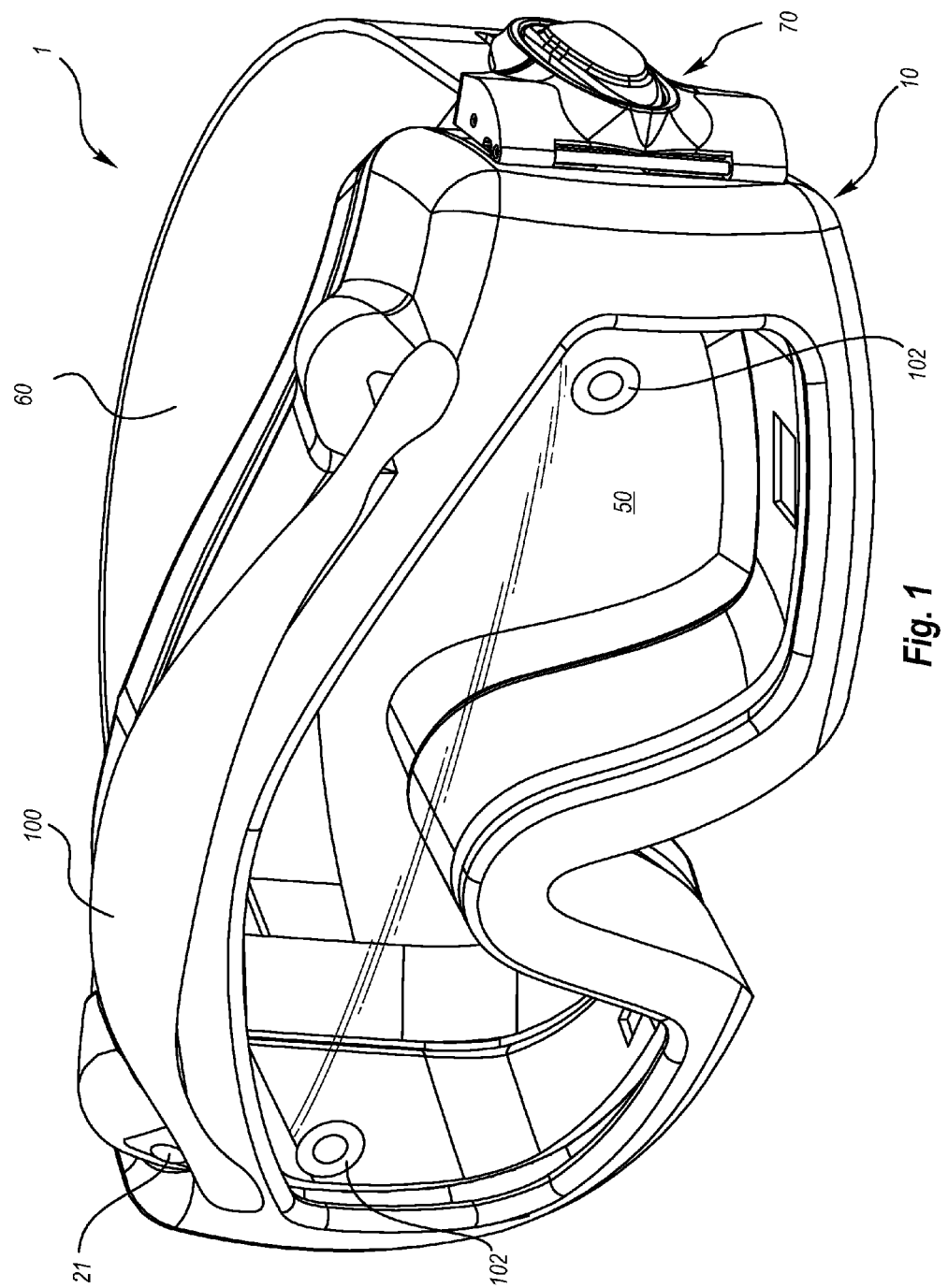
FIG. 1 is a top, right, front perspective view of a goggles implementation.
Figure 2:
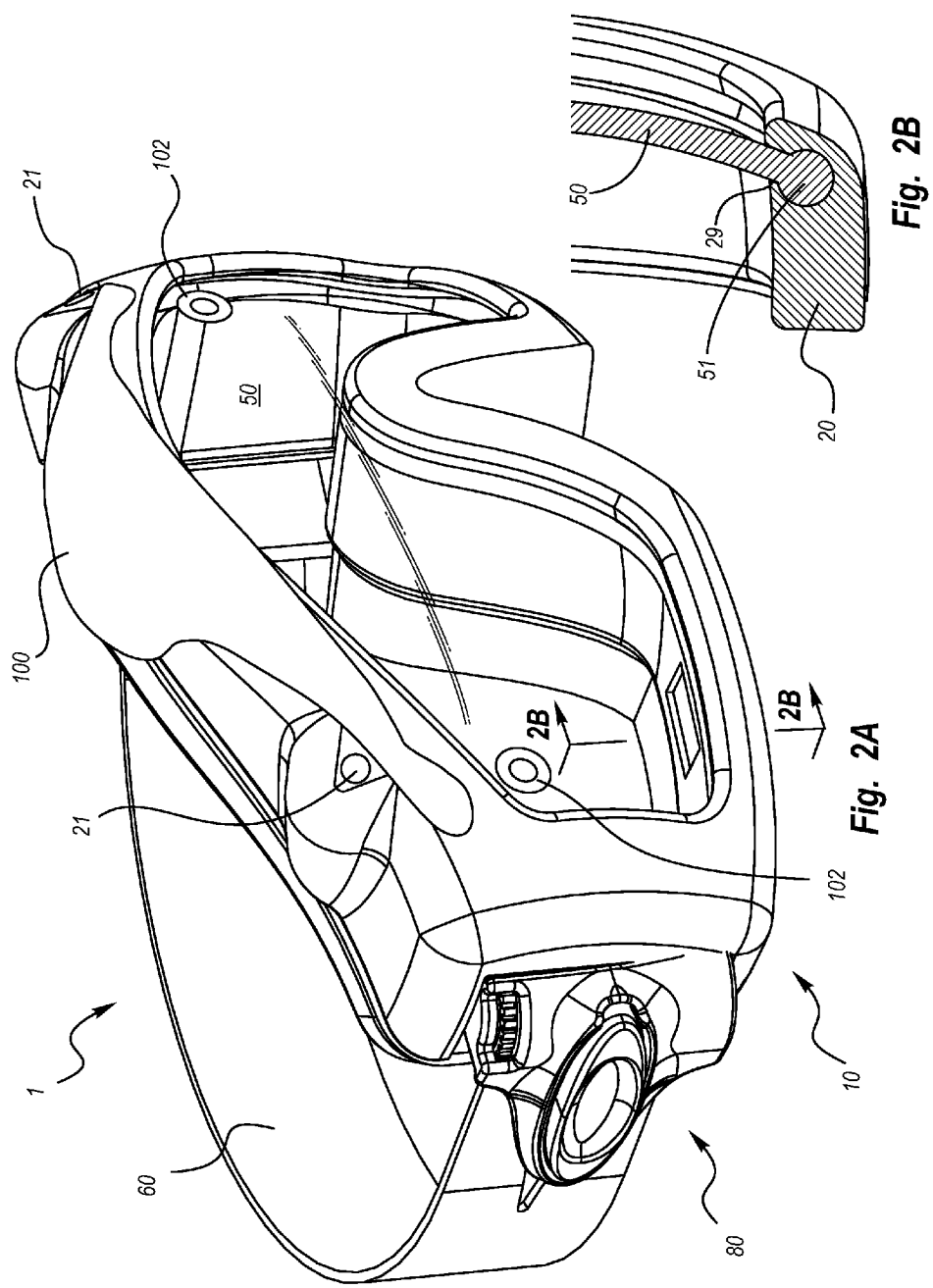
FIG. 2A is a top, left, front perspective view of the goggles implementation of FIG. 1.
FIG. 2B is a cross-sectional view of the goggles implementation of FIG. 1 taken along line 2B-2B.
Figure 3:
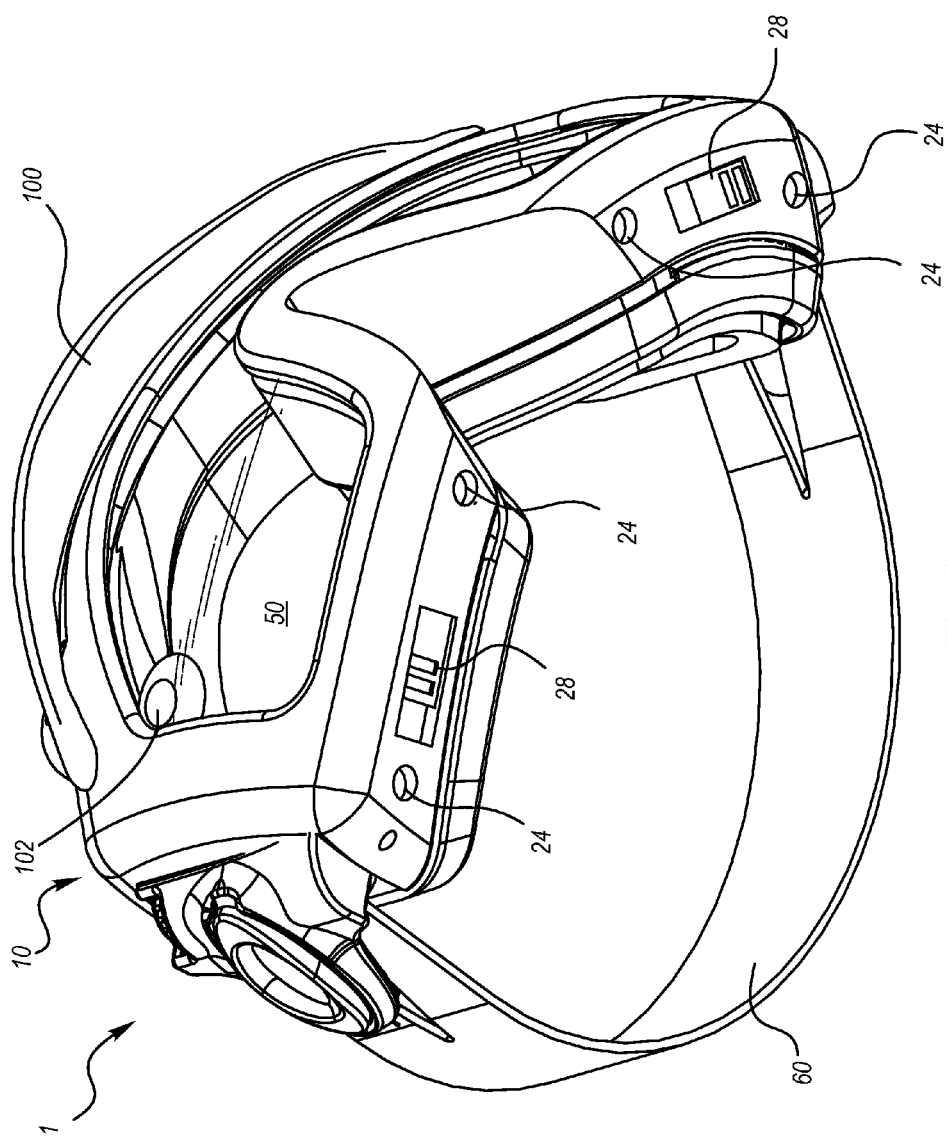
FIG. 3 is a bottom, left, front perspective view of the goggles implementation of FIG. 1.
Figure 4:
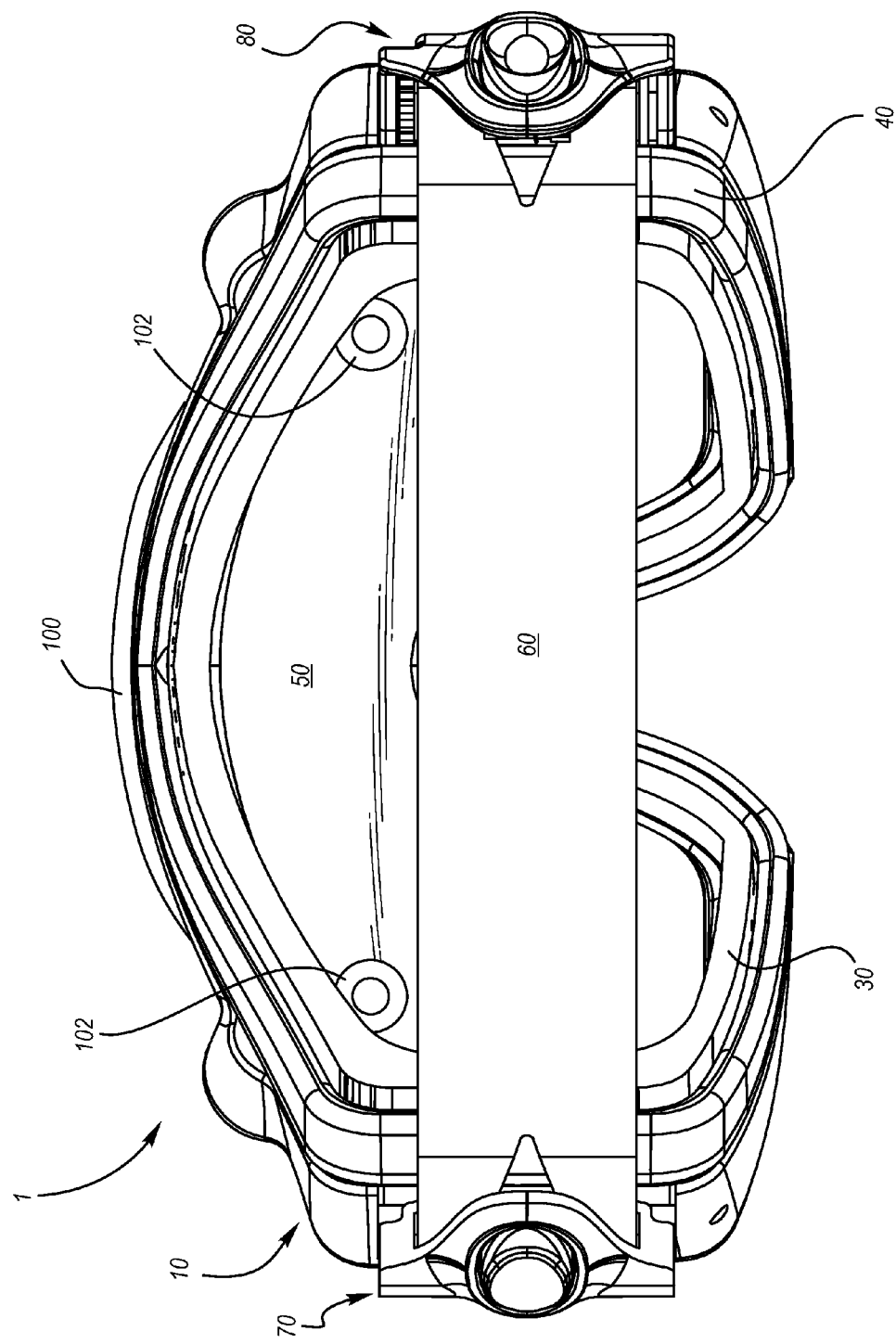
FIG. 4 is a rear view of the goggles implementation of FIG. 1.
Figure 5:
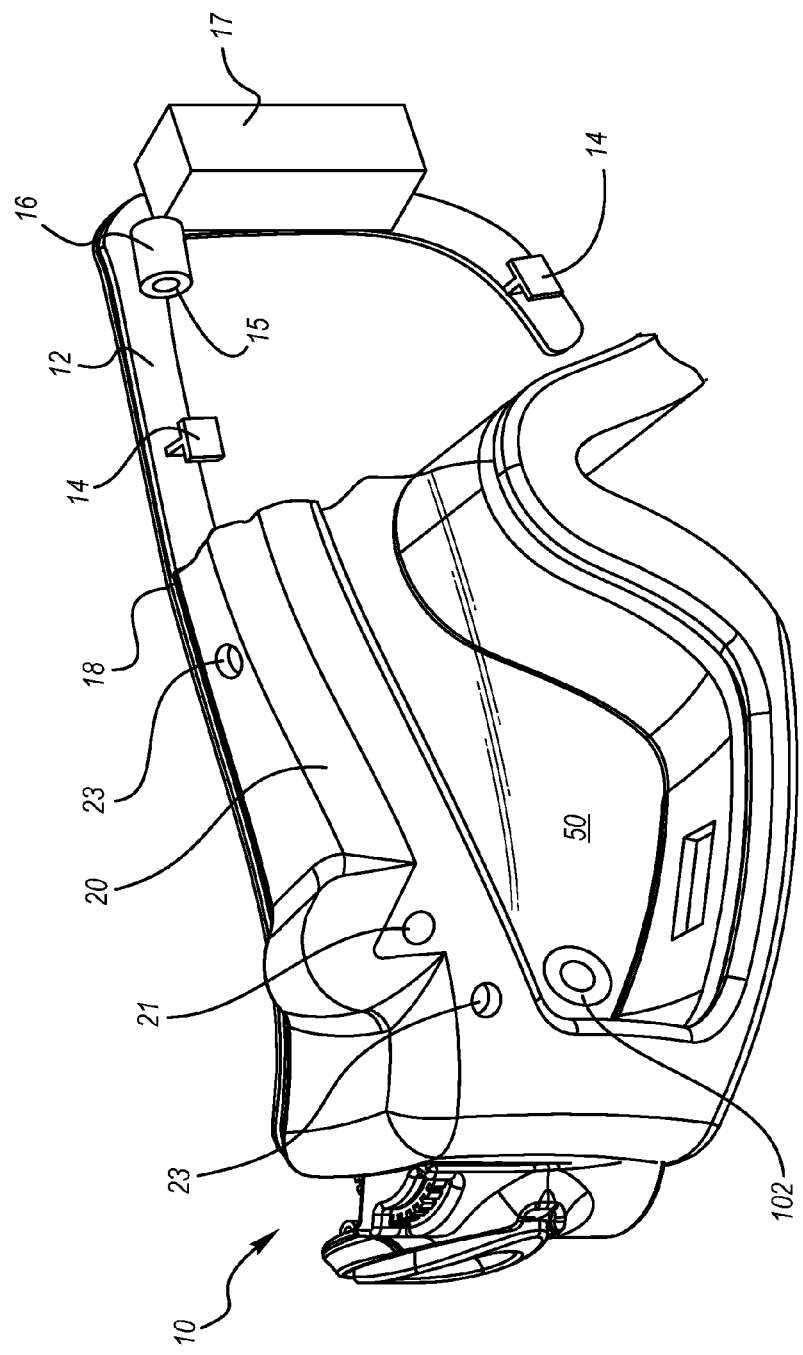
FIG. 5 is a broken-away, top, left, front perspective view of a frame assembly of the goggles implementation of FIG. 1 with part of the over mold member and lens removed.
Figure 6:
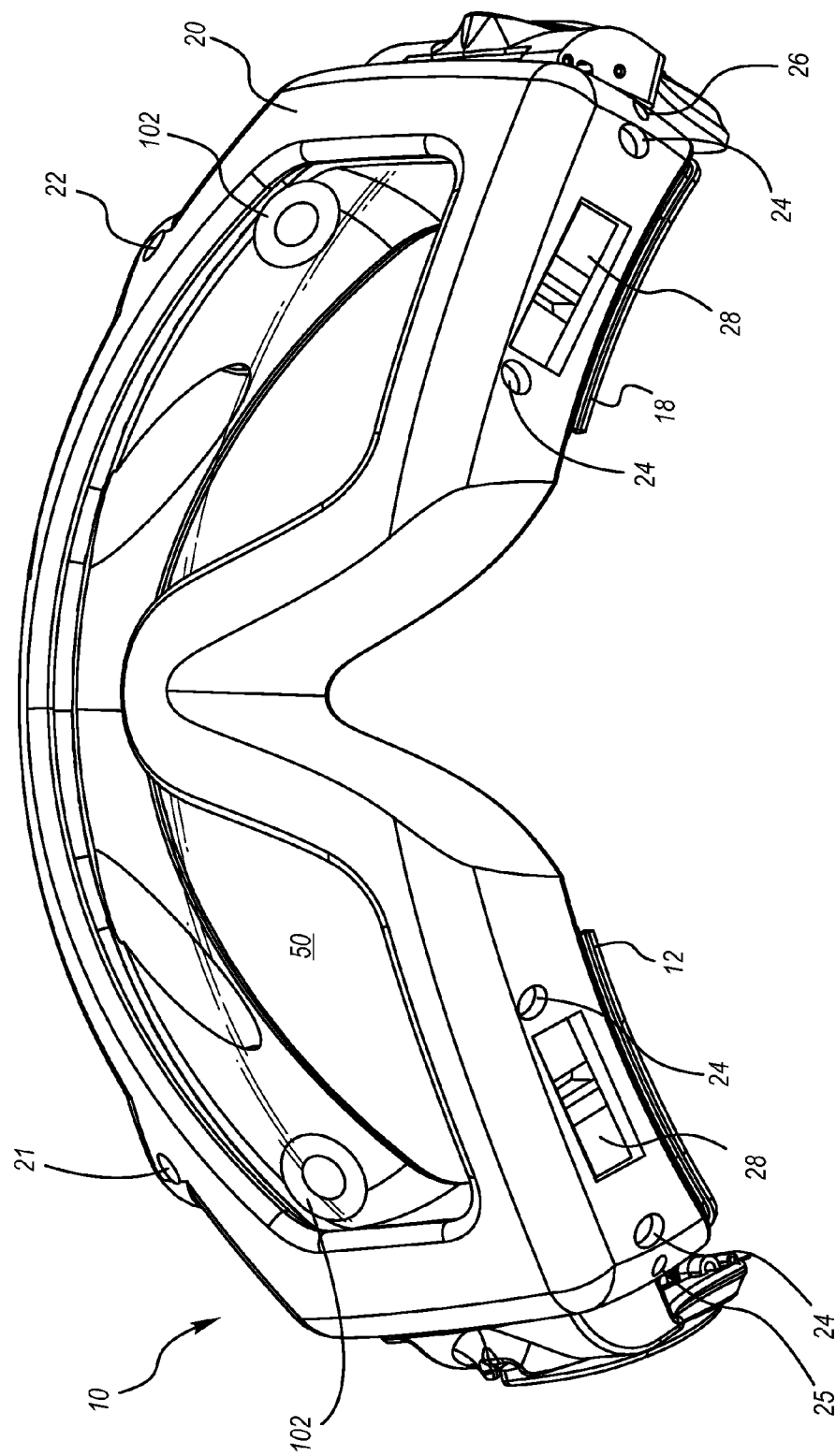
FIG. 6 is a bottom, front perspective view of the frame assembly of the goggles implementation of FIG. 1.

This document features implementations of eye, face, and head wear. There are many features of such implementations disclosed herein, of which one, a plurality, or all features or steps may be used in any particular implementation.

In the following description, reference is made to the accompanying DRAWINGS which form a part hereof, and which show by way of illustration possible implementations. It is to be understood that other implementations may be utilized, and structural, as well as functional and procedural, changes may be made without departing from the scope, applicability or configuration of this document in any way. As a matter of convenience, various components will be described using exemplary materials, sizes, shapes, dimensions, and the like. However, this document is not limited to the stated examples and other configurations are possible and within the teachings of the present disclosure. As will become apparent, changes may be made in the function and/or arrangement of any of the elements described in the disclosed exemplary implementations without departing from the spirit and scope of this disclosure.

There are a variety of implementations of eye, face, and head wear. Implementations of eye, face, and head wear may generally comprise at least one semipermeable membrane vent coupled to or integral with a lens, shield, and the like surface (or frames surrounding, integrating, associated with, and the like such surfaces) of an eye or face wear product, such as goggles, helmets, face shields (stand alone, as part of helmets, etc.), and the like for example. The microporous structure of such a semipermeable membrane allows for the free passage of gases and vapors while at the same time preventing water, dust and salt crystals from entering.

For example, at least one vent may be incorporated into the frame of eye or face wear for military/ballistic applications. As another example, for sporting goods applications, vents may be provided in the top corners of the lens for example. Any combination of vents will prevent goggle or shield fogging, make goggles, shields, helmets, and the like water proof for up to a min/max of 3 minutes, possibly up to 5, for example and make goggles, helmets, shields, and the like dust proof (and the vents can just be washed out).

The at least one vent may be formed of expanded polytetrafluoroethylene (ePTFE) for example. One particular example of such a vent is a GORE™ Protective Vent. GORE™ Protective Vents are the leading solution for pressure equalization (rapid equalization of pressure to reduce stress on enclosure seals), condensation reduction (reliable hydrophobic and oleophobic action to protect from water, salts and other corrosive liquids), venting and acoustic protection, superior airflow, and installation and maintenance. GORE™ Protective Vents provide a barrier against liquid, dust and dirt, while allowing for breathing during changing environmental conditions.

GORE™ Protective Vents incorporate a membrane of expanded polytetrafluoroethylene (ePTFE) (GORE-TEX® membrane). GORE™ Protective Vents can be designed with a variety of specific properties for maximum performance in any venting application. GORE-TEX® membranes contain over 9 billion microscopic pores per square inch. These pores are 20,000 times smaller than a water droplet, but 700 times larger than a water vapor molecule, which makes the GORE-TEX® membrane completely waterproof from the outside, while allowing perspiration to escape from the inside. An oleophobic, or oil-hating, substance is integrated into the membrane, preventing the penetration of body oils and insect repellent that could otherwise affect the membrane. No external moisture can penetrate the membrane. Perspiration can easily evaporate out through the membrane. Breathability is provided for, but wind stays out.

GORE™ Protective Vents come in a variety of product forms, including screw-in vents, press-fit vents, snap-in vents, o-rings, adhesive vents and acoustic vents.

Thus, vents can be made in any size, shape, and the like, and not only can be included in new locations on the frame or on a lens or shield, but can also be in other openings in the frame, under any existing/standard foam vents stuck to the frame for example.

Implementations of at least eye wear (and even some implementations of face wear that include straps such as chin straps or other straps) may further generally comprise a split strap design. Such a design provides a wide "anchor" to a goggle frame for example, which spreads out "pull' on the frame/lens, reducing goggle/helmet/shield squeeze. Whether split or not, such straps may be coupled to or over-molded onto the sub-frame.

The split strap may be formed of a thermoplastic elastomer (TPE) for example, which would allow for 3D textural designs on the strap (such as diamond plate texture and virtually any other type of texture for example). TPEs are a class of copolymers or a physical mix of polymers (usually a plastic and a rubber) that consist of materials with both thermoplastic and elastomeric properties. While most elastomers are thermosets, thermoplastics are in contrast relatively easy to use in manufacturing, for example, by injection molding. TPEs show both advantages typical of rubbery materials and plastic materials. The principal difference between thermoset elastomers and thermoplastic elastomers is the type of crosslinking bond in their structures. In fact, crosslinking is a critical structural factor that contributes to impart high elastic properties. The crosslink in thermoset polymers is a covalent bond created during the vulcanization process. On the other hand the crosslink in thermoplastic elastomer polymers is a weaker dipole or hydrogen bond or takes place in one of the phases of the material. In order to qualify as a TPE, a material must have these three essential characteristics: The ability to be stretched to moderate elongations and, upon the removal of stress, return to something close to its original shape; Processable as a melt at elevated temperature; and Absence of significant creep.

There are six generic classes of TPEs generally considered to exist commercially. They are styrenic block copolymers, polyolefin blends, elastomeric alloys (TPE-v or TPV), thermoplastic polyurethanes, thermoplastic copolyester and thermoplastic polyamides. Examples of TPE products that come from block copolymers group are Arnitel (DSM), Engage (Dow chemical), Hytrel (Du Pont), Kraton (Shell chemicals), Pebax (Arkema), Pellethane, Riteflex (Ticona), Styroflex (BASF) and more. While there are now many commercial products of elastomer alloy, these include: Alcryn (Du Pont), Dryflex, Evoprene (AlphaGary), Forprene, Geolast (Monsanto), Mediprene, Santoprene and Sarlink (DSM).

One particular example of a TPE material useful for eye, face, and head wear implementations is VERSAFLEX™ OM 9-802CL manufactured by PolyOne Corporation. VERSAFLEX™ OM 9-802CL has superior properties versus latex and other materials.

The membrane vents and the strap implementations discussed above could each be provided as a kit for retrofitting existing eye, face, and head wear (e.g., replacing straps) as opposed to just being part of an OEM eye or face or head wear product.

Other implementations of eye, face, and head wear could further include TPE over-molded (3-D texture potential, multi-color, nonglare, etc.) onto an Acrylonitrile-Butadiene-Styrene (ABS) or polycarbonate (PC) sub frame and/or PC lens for replaceable or permanent attachment of the frame to the lens. This arrangement (i.e., the sub frame) would provide a rigid but flexible frame for mounting items. This arrangement (i.e., the over molded TPE frame for example) would also eliminate frame to ear separation, dust/moisture entry, goggle squeeze/pressure, and the like. This arrangement (i.e., both the sub frame and over molded frame) would also provide increased resistance to crushing, increased shock absorption, increased insulation (no noise, impacts, more resilient), and the like.

Having such a sub-frame (in addition to the over-molded member) also allows for the addition/installation of add on technologies to a goggle frame for example, such as: a strap ratchet assembly on one or both sides (symmetrical pressure) (e.g., a strap ratchet may be coupled to, removably coupled to, over-molded, etc. to sub-frame implementations for example, or a strap ratchet may be adjustable (e.g., 5 way adjustability) and can be used with existing vinyl frames, or sub-frame implementations (e.g., adjusts simply with a wing nut, slots on the frame or sub-frame, and any number of spacers for example to allow custom interfacing with helmets, goggles, and the like)); a weather proof storage compartment on one or both sides; a mount for a GPS unit, etc. or various Bluetooth products, a camera, a heads up display, an LED light, a fan, a motor, etc., and/or any combination of the foregoing. A pump (manual or electric) may also be supported for inflating a face seal or gasket (over, under, or around the existing foam seal or gasket if any so the inflatable seal or gasket can make a dust proof seal all around a person's face). Even batteries or a solar power unit could be supported for powering a ratchet spool assembly or an air pump for a face seal or gasket or a light or camera for example. The sub-frame could also be perforated at the forehead area for example, which allows a ePTFE (e.g., removable strips) to be installed therein so that the outside air can help wick away perspiration, etc. from a persons forehead out through any foam sleeve, the ePTFE, and the perforated frame.

Furthermore, TPE could just be over-molded onto the lens. This would allow for increased interchangeability of lenses; the incredibly resilient TPE (e.g., VERSAFLEX™ OM 9-802CL has 1100% elongation) over-molded on the lens, or over-molded on the frame and the lens, will better load a lens for changeability as it will suck down onto/over the lens. Such a TPE over-molded frame, having resiliency/memory, allows lens edges to be beaded/bulbous all the way around for example (versus being flat). This allows for a stronger lens with a better seal.

Other implementations of eye, face, and head wear could further include soft/medium/hard sub-frames for pointy face people, normal people, and flat face people. All that is required is to vary the thickness of the ABS or PC sub-frame and over mold the sub-frame with TPE for example.

Other implementations of eye, face, and head wear for ballistic applications for example could further include a rotatable air vent or a rectangular slide/vent on the bottom, top, and/or side edge of the sub-frame. ePTFE (e.g., tear off strips) can be used in such vents as well for example.

Even other implementations of eye, face, and head wear could further include insert points at strategic positions around the frame for mounting a visor and/or a face shield to goggles for example.

Still other implementations of eye, face, and head wear could further include inflatable face seals or gaskets (over, under, or around the existing foam seal or gasket if any so the inflatable seal or gasket can make a dust proof seal all around a person's face).

Yet even other implementations may have just partial inflatable face seals or gaskets (e.g., an inflatable nose seal or gasket over, under, or around the existing foam seal or gasket if any so the inflatable nose seal or gasket can make a dust proof seal and accommodate the huge varieties of noses).

Other implementations may include or combine one or more or all of the forgoing features discussed in the foregoing implementations.

Further Implementations

Many implementations of eye, face, and head wear are possible for a wide variety of applications as previously described.

Notwithstanding and for the exemplary purposes of this disclosure, an implementation of a particular eye wear is shown in FIGS. 1-11B. Goggles include many of the features previously described. Generally, goggles 1 include frame assembly 10, foam face seal 30, inflatable seal 40, lens 50, strap 60, pump assembly 70, spool assembly 80, visor 100, and semipermeable membrane vents 102 and 104.

Frame assembly 10 includes sub-frame 12 and member 20 over-molded onto sub-frame 12. Sub-frame 12 includes over-mold attachment supports 14, vent mount 16 with opening 15, storage compartment 17, and inflatable face seal attachment member 18.

Member 20 over-molded onto the sub-frame 12 may be formed of TPE. The TPE may be VERSAFLEX™ OM 9-802CL. Member 20 over-molded onto the sub-frame may also be over-molded onto an edge of lens 50. Member 20 includes vent ports 21, visor snap in holes 23 (optional), face shield snap in holes 24 (optional), pin holes 25 and 26, and sliding air intake vents 28. Sliding air intake vents 28 may be included in a bottom of member 20 for example. Semipermeable membranes may be incorporated into sliding air intake vents 28.

Foam face seal 30 couples to inflatable seal 40. Inflatable seal 40 is coupled to sub-frame 12. Specifically, inflatable face seal 40 has a channel 42 defined therein that removably receives attachment member 18 of sub-frame 12. Inflatable face seal 40 further comprises air line 44 that couples into storage compartment 17 through hole 13.

Lens 50 can be removably coupled to frame 10. Specifically, the edge of lens 50 may be inserted into channel 29 defined in member 20. Lens 50 may have a beaded or bulbous edge 51. Lens 50 defines vent mount 52 apertures partially there through in corners of lens 50.

Strap 60 may be over-molded to the sub-frame 12. Or strap 60, as depicted, can be attached to spool assembly 80 at one end and pump assembly 70 at its other end. Strap 60 may have split ends 62 and 64 that couple with (e.g., receive there through) pins 92 and 93 respectively.

Pump assembly 70 is coupled to storage compartment 17 via a retention pin 90 and hinge pin 91 through hole 78. Pin 92 is coupled in hole 76. Pump assembly 70 includes inflation pump 72 in fluid communication with connection port 74, which fluidly communicates and couples with air line 44 to inflate seal 42 when pump 72 is repeatedly depressed. Pump 72 may be depressed and held to deflate seal 42.

Spool assembly 80 adjusts the strap 60. Alternatively, two strap spool assemblies could be included to provide symmetrical strap 60 adjustment (one may be coupled to one side of sub-frame 12 and the other may be coupled to the opposing side of sub-frame 12).

Strap spool assembly 80 is coupled to strap 60 and sub-frame 12. Specifically, strap spool assembly 80 is coupled to sub-frame 12 via a retention pin 90 through spool 81. Pin 93 is coupled in holes 88 and 89 of spool 81. Strap spool assembly 80 includes spool 81, strap winding members 82 and 83, ratchet stop 84, thumb wheel 85, strap tension release 86, and locking spring 87. The thumbwheel 85$n$ is rotated in one direction to tension strap 60 by winding end 64 around members 82 and 83. Locking spring 87 holds release 86 against ratchet stop 84 so tension is maintained in strap 60. When tension is to be released, release 86 is lifted away from stop 84 and the tension in strap 60 unwinds strap end 64 from spool 81.

Visor 100 may be removable. For example, visor 100 may include members that removably snap into holes 23 of member 20.

Semipermeable membrane vents 102 and 104 are installed into mount aperture 52 and openings 15 of vent mounts 16, respectively. Semipermeable membrane vents 102 and 104 and other similar vents may be installed in other locations on frame 10 and/or lens 50 as well. Semipermeable membrane vents 102 and 104 may be formed of expanded polytetrafluoroethylene, and may be a GORE™ Protective Vent for example. Other semipermeable membranes could just be swatches or strips of expanded polytetrafluoroethylene.

Figure 12:
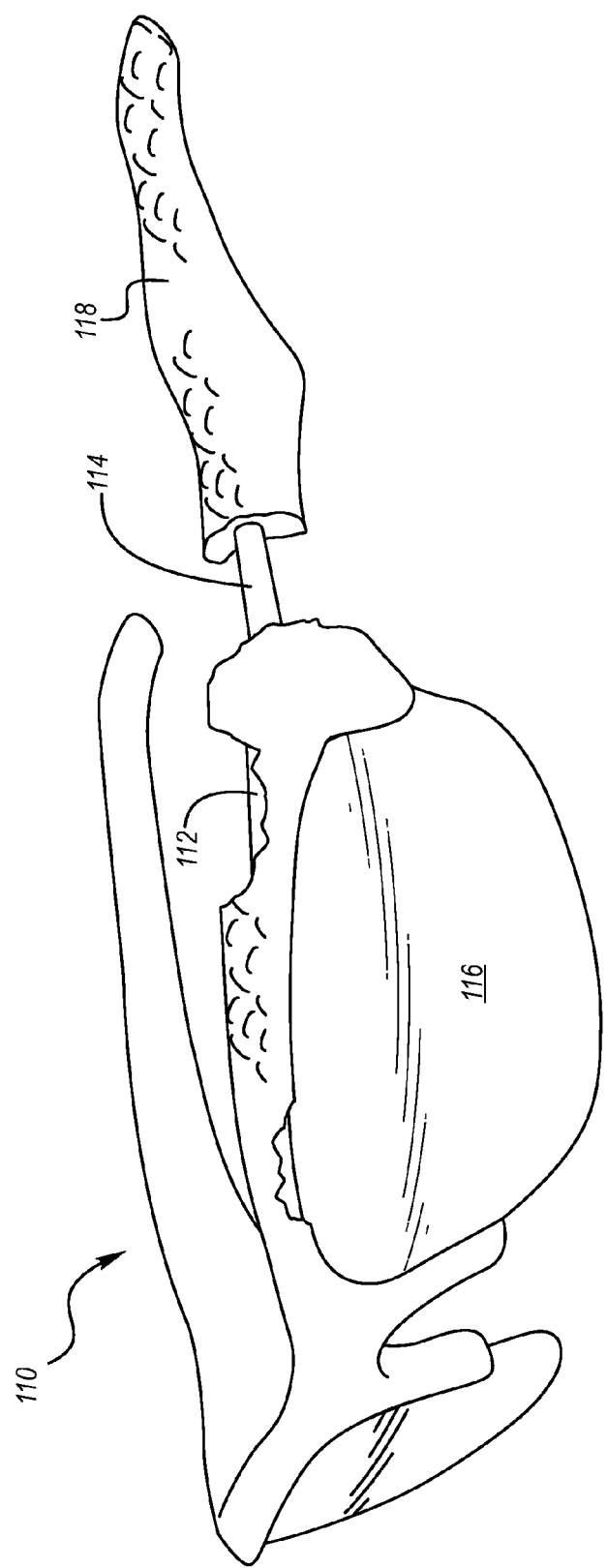
FIG. 12 is a broken-away, front perspective view of a sunglasses implementation with part of the over mold member removed.

For the exemplary purposes of this disclosure, another implementation of a particular eye wear is shown in FIG. 12. Sunglasses 110 include some of the features previously described. Specifically, sunglasses 110 include a frame 112 and temples 114. Over-molded onto both temples 114 and frame 112 is member 118. Member 118 may be TPE (such as VERSAFLEX™ OM 9-802CL) and may have a three-dimensional texture. Member 114 is both over-molded onto temples 114 and frame 112, as well as over-molded onto the edges of lenses 116. Alternatively, member 114 could be over-molded onto just temples 114, just frame 112, just the edges of lenses 116, or some combination thereof.

Figure 13:
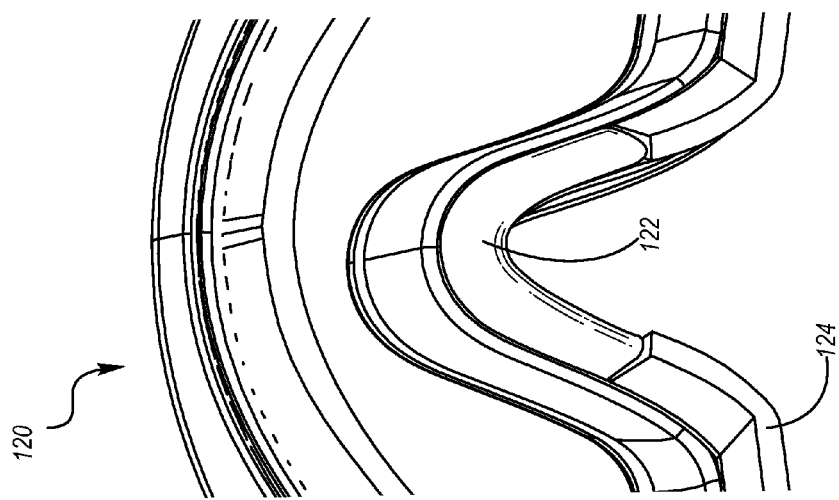
FIG. 13 is a broken-away, front perspective view of another goggles implementation.

For the exemplary purposes of this disclosure, another implementation of a particular eye wear is shown in FIG. 13. Goggles 120 include some of the features previously described. The principle difference is the inclusion of an inflatable nose seal 122. Inflatable nose seal 122 is similar to seal 42 as previously described. Inflatable nose seal 122 may operate like seal 42 as well, though it may be set up to operate differently. Inflatable nose seal 122 may be coupled to the frame (e.g., either a sub-frame or an over-molded member) at the frame's bridge. Inflatable nose seal 122 may be integrated into a another face seal, or may be separate but abutting a the other face seal, such as foam seal 124.

Figure 14:
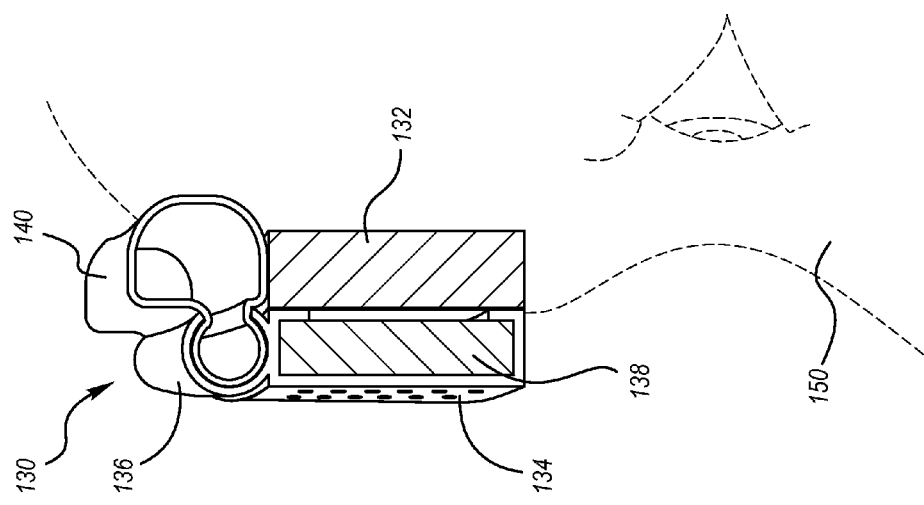
FIG. 14 is a cross-sectional, perspective view of still another goggles implementation in use.

For the exemplary purposes of this disclosure, another implementation of a particular eye wear is shown in FIG. 14. Goggles 130 include some of the features previously described. The principle difference is the inclusion of a perforated forehead section 134 and a semipermeable membrane vent 138 disposed therein. Goggles 130 may include many features common to goggles and some of the features disclosed with goggles 1. However, goggles 130 specifically include perforated forehead section 134 and a semipermeable membrane vent 138 disposed therein. The perforated forehead section 134 may be a channel member, the walls of which being inwardly flanged. The base of the channel member may be perforated with holes to allow air and fluids in and out. Semipermeable membrane vent 138 may be removably disposed in the channel member. Semipermeable membrane vent 138 may be a strip of expanded polytetrafluoroethylene for example. Abutting the channel member and Semipermeable membrane vent 138 can be a foam seal 132. Another seal 140, such as an inflatable seal, may be coupled to attachment member 136. As user 150 sweats, outside air can help wick away perspiration, etc. from the forehead of person 150 out through foam sleeve 132, the ePTFE membrane 138, and perforated frame 134.

Further implementations are in the CLAIMS.

Specifications, Materials, Manufacture, Assembly

It will be understood that implementations are not limited to the specific components disclosed herein, as virtually any components consistent with the intended operation of eye, face, and head wear may be utilized. Accordingly, for example, although particular components and so forth, are disclosed, such components may comprise any shape, size, style, type, model, version, class, grade, measurement, concentration, material, weight, quantity, and/or the like consistent with the intended operation of eye, face, and head wear. Implementations are not limited to uses of any specific components, provided that the components selected are consistent with the intended operation of eye, face, and head wear.

Accordingly, the components defining any implementation may be formed of any of many different types of materials or combinations thereof that can readily be formed into shaped objects provided that the components selected are consistent with the intended operation of an apparatus for holding a portable media device. For example, the components may be formed of: ePTFE (e.g. GORE-TEX®); Elastomers (such as TPE (e.g. VERSAFLEX™ OM 9-802CL), etc.); polymers such as thermoplastics (such as ABS, Fluoropolymers, Polyacetal, Polyamide; Polycarbonate, Polyethylene, Polysulfone, and/or the like), thermosets (such as Epoxy, Phenolic Resin, Polyimide, Polyurethane, Silicone, and/or the like), any combination thereof, and/or other like materials; rubbers (synthetic and/or natural), and/or other like materials; glasses (such as fiberglass), carbon-fiber, aramid-fiber, any combination thereof, and/or other like materials; composites and/or other like materials; metals, such as zinc, magnesium, titanium, copper, iron, steel, carbon steel, alloy steel, tool steel, stainless steel, spring steel, aluminum, any combination thereof, and/or other like materials; alloys, such as aluminum alloy, titanium alloy, magnesium alloy, copper alloy, any combination thereof, and/or other like materials; any other suitable material; and/or any combination thereof.

Various implementations may be manufactured using conventional procedures as added to and improved upon through the procedures described here. Some components defining implementations may be manufactured simultaneously and integrally joined with one another, while other components may be purchased pre-manufactured or manufactured separately and then assembled with the integral components.

Manufacture of these components separately or simultaneously may involve extrusion, pultrusion, vacuum forming, injection molding, blow molding, resin transfer molding, over- or co-molding, casting, forging, cold rolling, milling, drilling, reaming, turning, grinding, stamping, cutting, bending, welding, soldering, hardening, riveting, punching, plating, and/or the like. If any of the components are manufactured separately, they may then be coupled with one another in any manner, such as with adhesive, a weld, a fastener (e.g. a bolt, a nut, a screw, a rivet, a pin, and/or the like), wiring, any combination thereof, and/or the like for example, depending on, among other considerations, the particular material forming the components.

Figure 7:
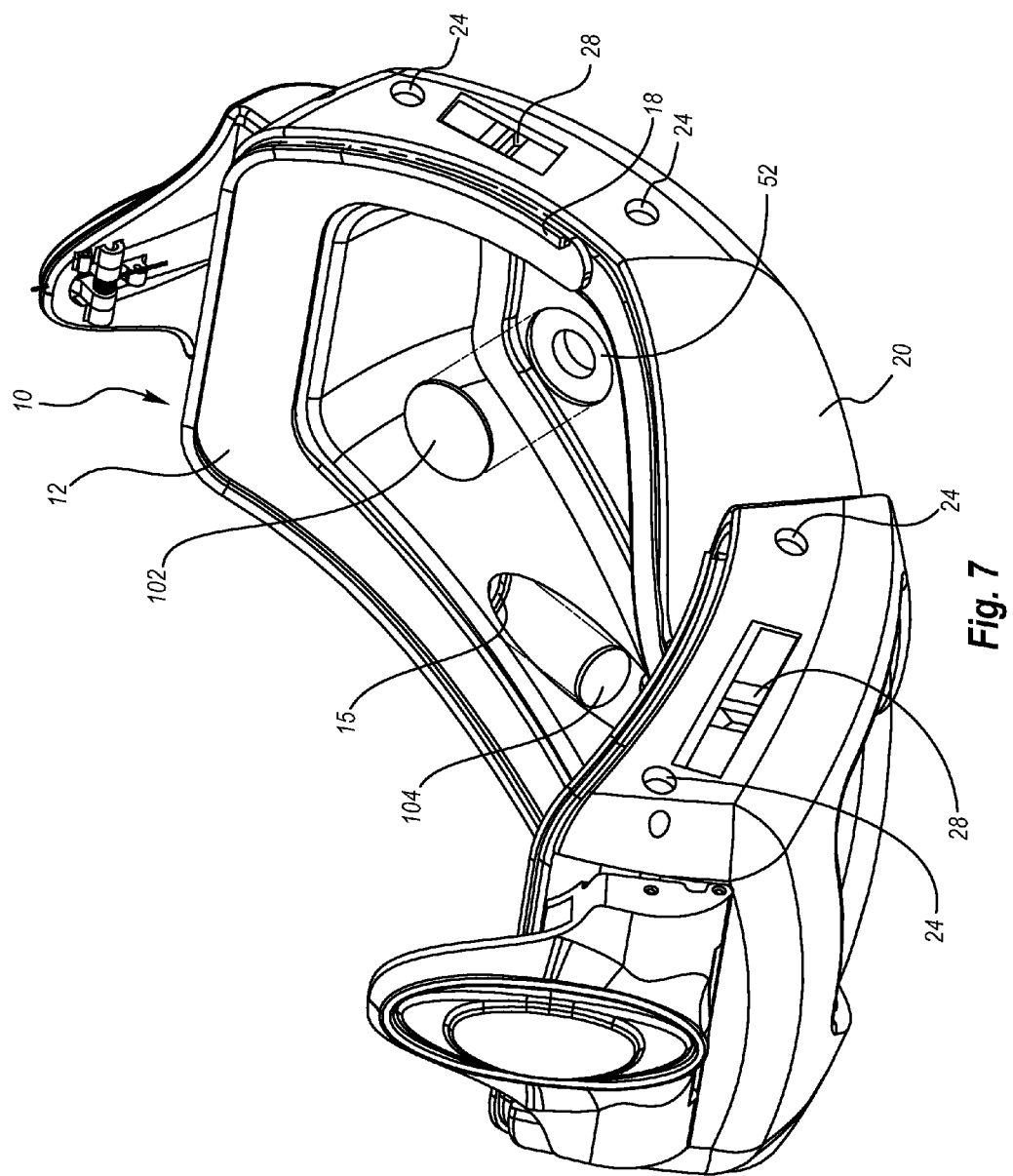
FIG. 7 is an exploded, rear perspective view of the frame assembly of the goggles implementation of FIG. 1.
Figure 8:
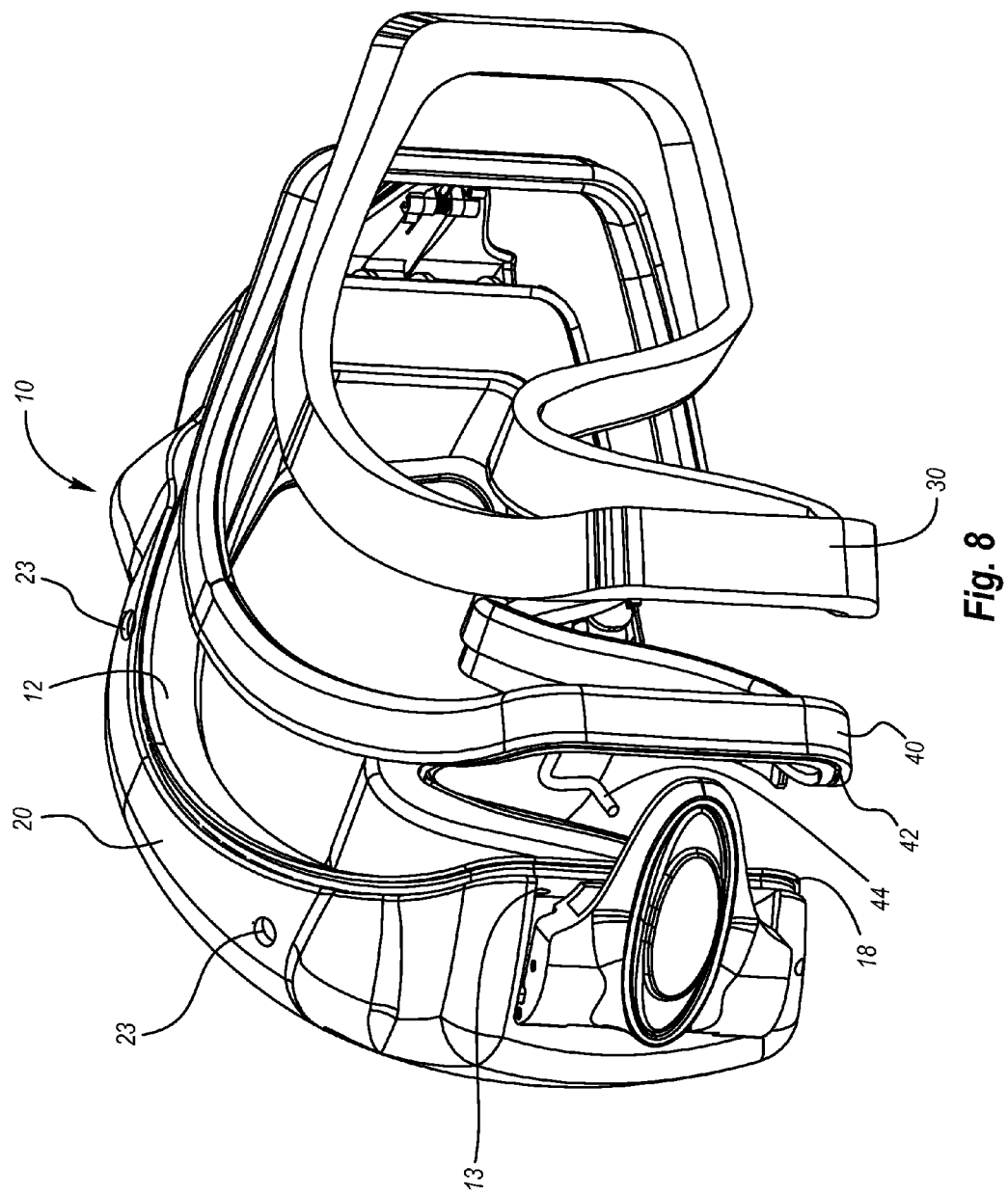
FIG. 8 is an exploded, rear perspective view of the goggles implementation of FIG. 1.
Figure 9:
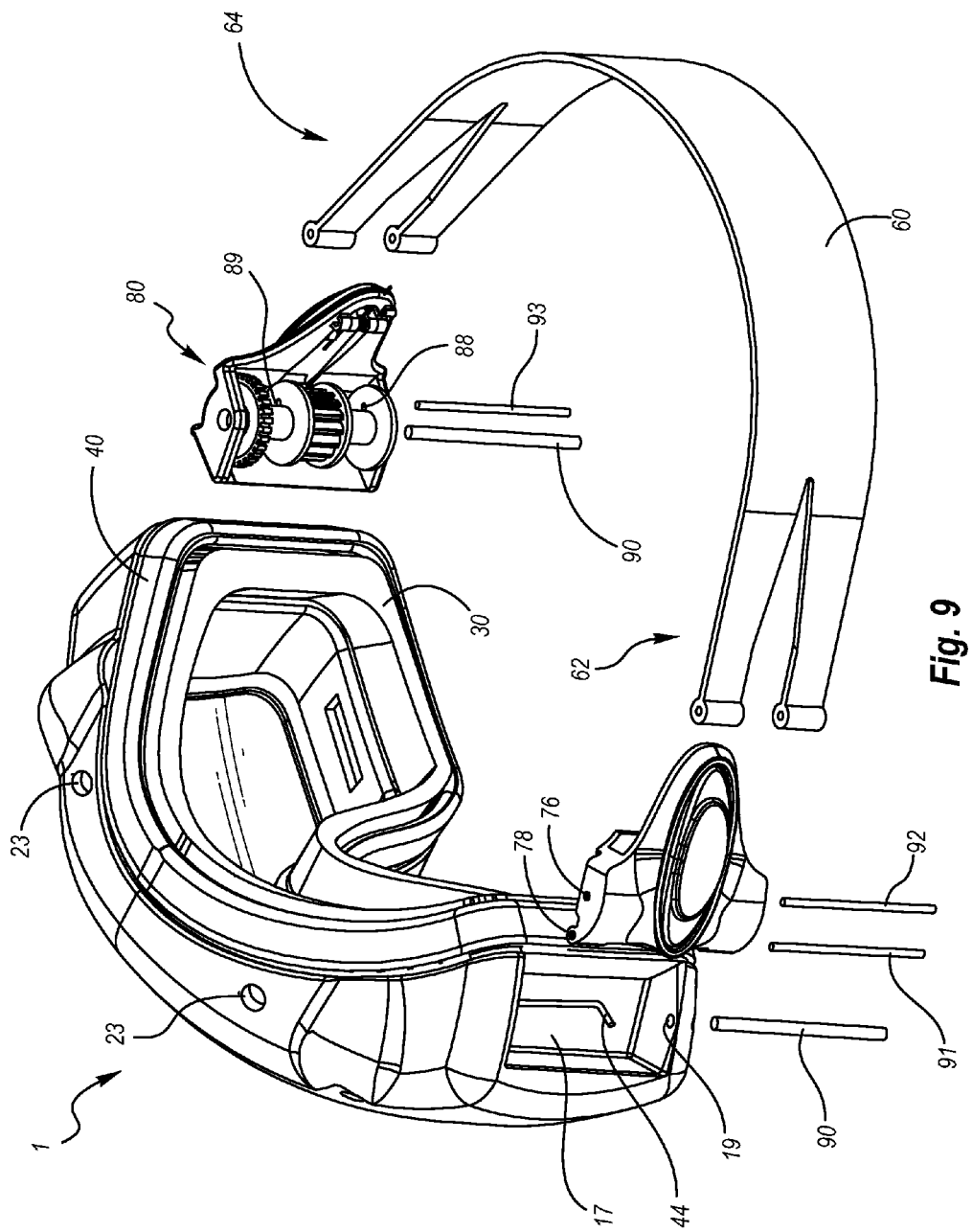
FIG. 9 is another exploded, rear perspective view of the goggles implementation of FIG. 1.

It will be understood that the assembly of implementations of eye, face, and head wear are not limited to the specific order of steps as disclosed in this document. Any steps or sequence of steps of the assembly or installation of implementations indicated herein are given as examples of possible steps or sequence of steps and not as limitations, since various assembly and installation processes and sequences of steps may be used. For example, goggles 1 may be assembled as depicted in the views of FIGS. 7-9.

Use

The aspects and implementations listed here, and many others, will become readily apparent to those of ordinary skill in the art from this disclosure. Those of ordinary skill in the art will readily understand the versatility with which this disclosure may be applied.

Implementations of eye, face, and head wear are particularly useful in consumer or sporting eye, face, and head wear applications, such as goggles or masks for racing, motocross, horse racing, swimming, scuba, snowmobiling, skiing, snowboarding, etc. However, implementations are not limited to uses relating to consumer or sporting eye, face, and head wear applications. Rather, any description relating to consumer or sporting eyewear applications is for the exemplary purposes of this disclosure, and implementations may also be used in a variety of eye, face, and head wear applications with similar results, such as sunglass applications, safety glass applications, laboratory applications, firefighter applications (Respirators), military/ballistics/police applications, helmet applications, face shield applications, and the like.

In places where the description above refers to particular implementations of eye, face, and head wear, it should be readily apparent that a number of modifications may be made without departing from the spirit thereof. The presently disclosed aspects and implementations are, therefore, to be considered in all respects as illustrative and not restrictive.

The invention claimed is:

1. One of eye, face, and head wear comprising: a frame assembly comprising: a sub-frame formed of at least one of Acrylonitrile-Butadiene-Styrene (ABS) material and polycarbonate material (PC); and a member over-molded onto the sub-frame; a lens coupled to the frame member over-molded onto the sub-frame; and at least one semipermeable membrane vent disposed in at least one of the frame assembly and the lens, the at least one semipermeable membrane vent formed of expanded polytetrafluoroethlene; a strap coupled to the sub-frame; and at least one strap spool assembly for adjusting the strap, the at least one strap spool assembly coupled to the strap and the sub-frame and comprising a spool, strap winding members, a ratchet stop, a thumb wheel, a strap tension release, and a locking spring.

2. The eye, face, and head wear of claim 1 further comprising at least one sliding air intake vent in a bottom of the frame assembly, and wherein the at least one semipermeable membrane vent is incorporated into the at least one sliding air intake vent.

3. The eye, face, and head wear of claim 1, wherein the at least one semipermeable membrane vent comprises at least a first semipermeable membrane vent disposed in the frame assembly and a second semipermeable membrane vent disposed in the lens.

4. The eye, face, and head wear of claim 1 wherein the member over-molded onto the sub-frame is formed of a thermoplastic elastomer.

5. The eye, face, and head wear of claim 1, wherein the member over-molded onto the sub-frame is also over-molded onto an edge of the lens.

6. The eye, face, and head wear of claim 1 further comprising an inflatable face seal coupled to the frame assembly.

7. The eye, face, and head wear of claim 6, further comprising a pump assembly coupled to the frame assembly, the pump assembly comprising an inflation pump in fluid communication with an air line operably coupled to the inflatable seal, wherein the inflatable seal inflates responsive to actuation of the inflation pump.

8. The eye, face, and head wear of claim 1 further comprising an inflatable nose seal coupled to the frame assembly.

9. The eye, face, and head wear of claim 1 wherein the frame assembly further comprises a perforated forehead section and a semipermeable membrane vent disposed therein.

* * * * *